(12) United States Patent
Fonteyn

(10) Patent No.: US 8,881,752 B1
(45) Date of Patent: Nov. 11, 2014

(54) SYSTEMS FOR CLEANING INSTRUMENTS

(71) Applicant: Stella Fonteyn, Little Falls, MN (US)

(72) Inventor: Stella Fonteyn, Little Falls, MN (US)

( * ) Notice: Subject to any disclaimer, the term of this patent is extended or adjusted under 35 U.S.C. 154(b) by 0 days.

(21) Appl. No.: 13/874,101

(22) Filed: Apr. 30, 2013

Related U.S. Application Data

(60) Provisional application No. 61/640,505, filed on Apr. 30, 2012.

(51) Int. Cl.
*B08B 3/12* (2006.01)
*B08B 6/00* (2006.01)
*B08B 3/02* (2006.01)

(52) U.S. Cl.
CPC .................................... *B08B 3/02* (2013.01)
USPC ...................................................... 134/198

(58) Field of Classification Search
None
See application file for complete search history.

(56) References Cited

U.S. PATENT DOCUMENTS 5,040,950 A * 8/1991 Dalquist et al. ............... 417/234

OTHER PUBLICATIONS iSoaker.com, http://www.isoaker.com/Armoury/Analysis/1996/super_soaker_xxp275.html, last visited, Oct. 14, 2013.*
iSoaker.com, http://www.isoaker.com/Armoury/Analysis/2007/super_soaker_aqsecretstrike.html, last visited, Oct. 14, 2013.*

* cited by examiner

*Primary Examiner* — Jason Ko
(74) *Attorney, Agent, or Firm* — Underwood & Associates, LLC

(57) ABSTRACT

Hand-held pumps are disclosed. In one embodiment, a hand-held pump is configured to produce a jet containing water, a sanitizing solution, or a combination thereof for the purpose of cleaning an object such as a medical device.

16 Claims, 4 Drawing Sheets

SYSTEMS FOR CLEANING INSTRUMENTS

CROSS-REFERENCE TO RELATED APPLICATIONS

This application claims priority to and the benefit of U.S. Provisional Patent Application No. 61/640,505, entitled "Systems for Cleaning Instruments" and filed on Apr. 30, 2012, the entire contents of which are incorporated by reference in their entirety as if fully set forth herein.

TECHNICAL FIELD

This disclosure relates to systems configured for cleaning foreign materials from instruments, especially instruments having small crevices, dimples, pores, or other, similar features such as medical or dental equipment.

BACKGROUND

A wide variety of instruments exist for use by health care professionals, including those for surgery, wound care and treatment, exploratory procedures, dentistry, and other applications. Medical instruments are sometimes designed and constructed for a specific purpose, e.g., cutting and dissecting, clamping, grasping and holding, suctioning, retracting, dilating, etc. Maintaining proper sterility of non-disposable instruments can be paramount in hospital and other clinical care settings where medical instruments are sometimes re-used after proper cleaning and sterilization techniques. Disease can be spread between patients if appropriate measures are not taken to thoroughly clean and disinfect instruments such as saws, scissors, bone chisels, endoscopes, and the like before they are reused on another patient.

Medical equipment can be prepared for re-use following a three step process including cleaning, disinfection, and sterilization. Cleaning is a macro-scale process that includes removing visible debris, blood, tissue, bone, and other, similar materials from the instrument. Disinfection commonly includes the application of chemicals or subjecting the instrument to physical processes capable of destroying pathogens. Sterilization commonly refers to processes that destroy all viable forms of microbial life, including bacterial spores by either physical or chemical processes and includes, for example, irradiation and autoclave methods.

Medical instruments can be very expensive to hospitals and clinics, therefore, they are often reused if it the risk of infection or disease transmission from one patient to another can be minimized. Thus, proper cleaning, disinfecting, and sterilization can not only reduce risk to the patient, but provide cost savings to hospitals and clinics.

SUMMARY

In general, devices for cleaning medical instruments are described. In one embodiment, such a device is a hand-held wand capable of producing strong, focused jets of cleaning solution or pure water. In this embodiment, the focused jet of water is emitted at a head portion of the wand and capable of driving bone, tissue, blood, and other bodily substances from small crevices and other areas of a medical instrument. In this embodiment, the head member also includes a shield configured to reduce the likelihood of splash-back when the operator is using the device.

In one exemplary aspect, a hand-held pump for cleaning foreign matter from an object is disclosed. The pump includes a pump housing that includes an internal pump capable of pumping water and soap solution from one or more supply reservoirs to a nozzle body. The nozzle body is capable of producing a jet for dislodging the foreign matter from the object, and the nozzle body is interchangeable with other, different nozzle bodies that produce jets having unique jet characteristics. The pump housing or the nozzle body can be configured to receive a reversibly-attachable splash guard to prevent the foreign matter from splashing on a user of the hand-held pump.

In one exemplary aspect, a hand-held, medical device cleaning system is disclosed. The cleaning system includes a pump housing itself including an internal pump capable of pumping a cleansing solution from a first inlet lumen to a nozzle body. The nozzle body is configured to produce a jet of the cleansing solution which is capable of removing foreign contaminants from the medical device.

In one embodiment, the medical device is an instrument used in medical or dental surgery.

In one embodiment, the nozzle body is configured to produce a jet of the cleansing solution having a jet cross-diameter from about 0.25 mm to about 5.0 mm. In various embodiments, the instrument is a scalpel, saw, drill bit, clamp, forceps, tweezers, retractor, needle driver, hemostat, scissors, catheter, mirror, probe, bur, excavator, burnisher, scaler, prosthodontic, elevator, or chisel.

In one embodiment, the pump housing is configured to reversibly couple with one of a plurality of nozzle bodies each capable of producing jets having unique jet characteristics. In a related embodiment, the pump housing includes a shoulder body on a distal end portion having a threaded bore configured to threadingly engage a correspondingly threaded proximal end portion of the nozzle body. In one embodiment, the pump housing includes a threaded shoulder body configured to threadingly engage a cap body of a nozzle turret. In one embodiment, the nozzle turret includes the cap body, and a plurality of unique nozzle bodies extending substantially perpendicularly from the cap body. The nozzle turret is configured to allow the cleansing solution to flow through a selected one of the plurality of nozzle bodies to produce the jet. In one embodiment, the plurality of nozzle bodies includes a first nozzle body configured to produce a straight stream; a second nozzle body configured to produce a fan-stream; and a third nozzle body configured to produce a pulsating straight stream. In one embodiment, the nozzle body includes a progressively narrowing interior lumen extending from a proximal portion of the nozzle body to a distal portion of the nozzle body where the jet emerges from the nozzle body. In one embodiment, the nozzle body includes a bend between the angles of about ninety (90) degrees and about thirty (30) degrees.

In one embodiment, the nozzle body is resiliently flexible.

In one embodiment, the pump housing or the nozzle body is configured to receive a reversibly-attachable splash guard configured to confine splashing of the cleansing solution or the foreign contaminants to the area of the nozzle body. In one embodiment, the splash guard is a dome-shaped shield configured to reversibly attach to the nozzle body, wherein a concave side of the shield faces a distal tip of the nozzle body.

In one embodiment, the cleaning system further includes a second lumen in fluid communication between a reservoir of a selected cleaning agent and the pump, and the first inlet lumen is connected to a water source. In one embodiment, the cleaning system further includes one or more selector bodies operably configured on the pump housing to control one or more of: the resulting temperature of the jet, the resulting force of the jet, or the concentration of the cleaning agent in the cleansing solution. In one embodiment, the one or more selector bodies is configured to selectively allow a user to choose between: a wash setting, wherein the jet is composed of water and the cleansing agent mixed in a selected ratio; a rinse setting, wherein the jet is composed of water only; and a pulse setting, wherein the jet is composed of either water only, or water plus the cleansing agent, and the jet is produced in a pulsating stream.

In one exemplary aspect, a medical instrument cleaning system is disclosed. The medical instrument cleaning system includes a hand-held housing, including a pump, first and second inlet lumens in fluid communication with the pump for receiving water and a selected cleansing agent respectively, and a shoulder body. The cleaning system further includes means for selectively producing a desired liquid jet from one of a plurality of nozzle bodies for cleaning the medical instrument.

In one embodiment, the cleaning system further includes one or more controls operable to selectively adjust the concentration of the cleansing agent in the liquid jet.

In one embodiment, the cleaning system further includes means for reducing the likelihood of splash-back of the liquid jet during cleaning of the medical instrument.

Certain advantages of the systems and methods include: the ability to focus a strong jet of cleaning solution onto targeted areas of a medical device for the purpose of removing foreign substances; a corresponding advantage of the systems and methods described herein is the ability to reuse medical instruments that may otherwise be discarded for lack of being able to remove small bits of foreign matter; a further advantage is a potential cost savings to a hospital or clinic in cleaning expenditures, as nurses, technicians, and other hospital employees can pre-clean an instrument to a greater extent than using brushes, bin washers, and other approaches; among others.

Unless otherwise defined, all technical and scientific terms used herein have the same meaning as commonly understood by one of ordinary skill in the art. Although methods and materials similar or equivalent to those described herein can be used in the practice or testing of any described embodiment, suitable methods and materials are described below. In addition, the materials, methods, and examples are illustrative only and not intended to be limiting. In case of conflict with terms used in the art, the present specification, including definitions, will control.

The foregoing summary is illustrative only and is not intended to be in any way limiting. In addition to the illustrative aspects, embodiments, and features described above, further aspects, embodiments, and features will become apparent by reference to the drawings and the following detailed description and claims.

DESCRIPTION OF DRAWINGS

The present embodiments are illustrated by way of the figures of the accompanying drawings in which like references indicate similar elements, and in which.

DETAILED DESCRIPTION OF ILLUSTRATIVE EMBODIMENTS

In one exemplary aspect, systems and methods are described for removing contaminants from medical instruments. In a preferred embodiment, a cleaning system includes a hand-held wand operably connected to a water source that is capable of producing a small, powerful jet of water or other cleaning solution for removing contaminants from medical devices having small crevices, apertures, protrusions, and the like. As used herein, "contaminants" can include gross contaminants such as blood, bone, tissue, and other substances that can adhere to various parts of medical and dental devices. As used herein, "devices" such as "medical devices" or "dental devices" can refer to any of a variety of devices used by health care practitioners, e.g., physicians, surgeons, medical assistants, and the like during a medical or dental procedure. A "procedure" can refer to, without limitation, operations on humans or other animals where various instruments are used for, e.g., cutting, sawing, drilling, or inserting a device into a patient's physiology. "Medical equipment" can refer to instruments such as those previously mentioned, including instruments used in dentistry.

Figure 1:
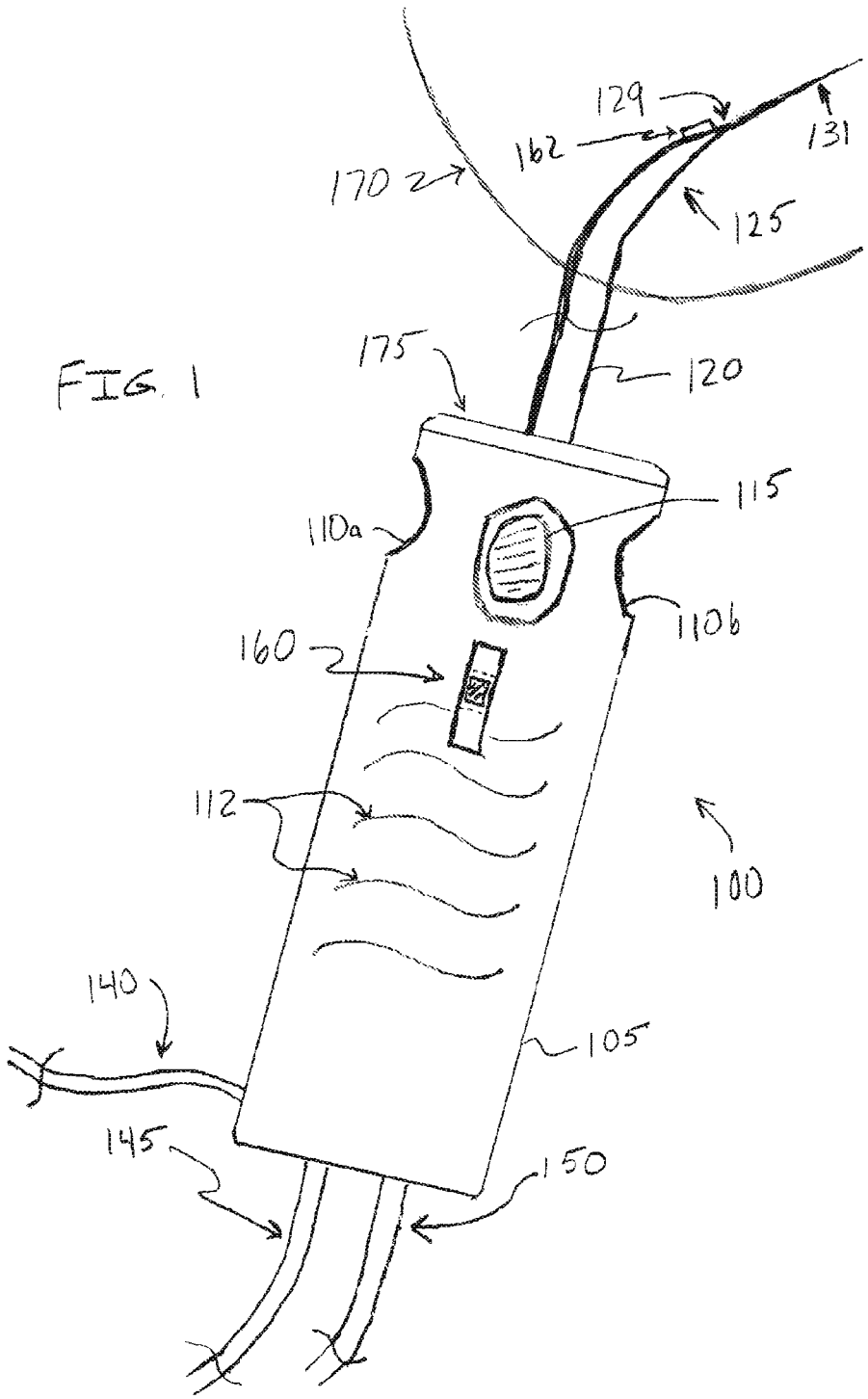
FIGS. 1-1A illustrate a cleaning device, according to one embodiment.

FIG. 1 is a system 100 for cleaning medical equipment according to one embodiment. The cleaning system 100 can be used for many purposes; however, in one exemplary aspect the device can be used for cleaning medical instruments. The cleaning device 100 is operable to produce a focused, powerful stream or jet of solution, e.g., water or cleaning solution that can be used to dislodge foreign contaminants such as blood, bone, or tissue from medical instruments after use.

In this embodiment, the cleaning device 100 includes a handle body 105 that can be ergonomically shaped according to preference, e.g., for comfort and convenience of the user. For example, in this embodiment, the handle body 105 includes two recesses defined by two concave wall portions 110a, 110b that can be engineered into the body 105 during manufacture, and provide a desired degree of ergonomic comfort.

In general, the handle body 105 can include one or more features for enhanced gripping ability and to reduce the likelihood of slippage from the user's hand during use. In this embodiment, a series of protruding ribs 112 (wherein only two ribs are specifically referred to by reference number 112 for clarity) can provide a textured surface to provide a better grip for the user. In this and other embodiments, the one or more features for enhanced gripping ability (e.g., the protruding ribs 112) can be integral with the material of the handle body 105, or they can be part of a separate housing, sleeve, or other structure that engages the handle body 105 and is held by friction, elastic tension, or other forces.

In this embodiment, the handle body 105 further includes an on/off switch 115 capable of powering the device 100 for use. The on/off switch 115 can be of the push-button type, a slide-switch, or any other configuration of on/off switch known in the art. In this embodiment, the on/off switch can be conveniently located near the location of the user's thumb as it is being held, providing easy on/off capabilities.

In this embodiment, a first supply tube 145 can be reversibly coupled to the handle body 105 for the purpose of transporting water or a cleansing solution from a storage tank (not shown in FIG. 1) to the handle body 105. A second, optional supply tube 150 can be reversibly coupled to the handle body 105 for the purpose of transporting soap, disinfectants, or other cleaning chemicals to the handle body 105.

Figure 1A:
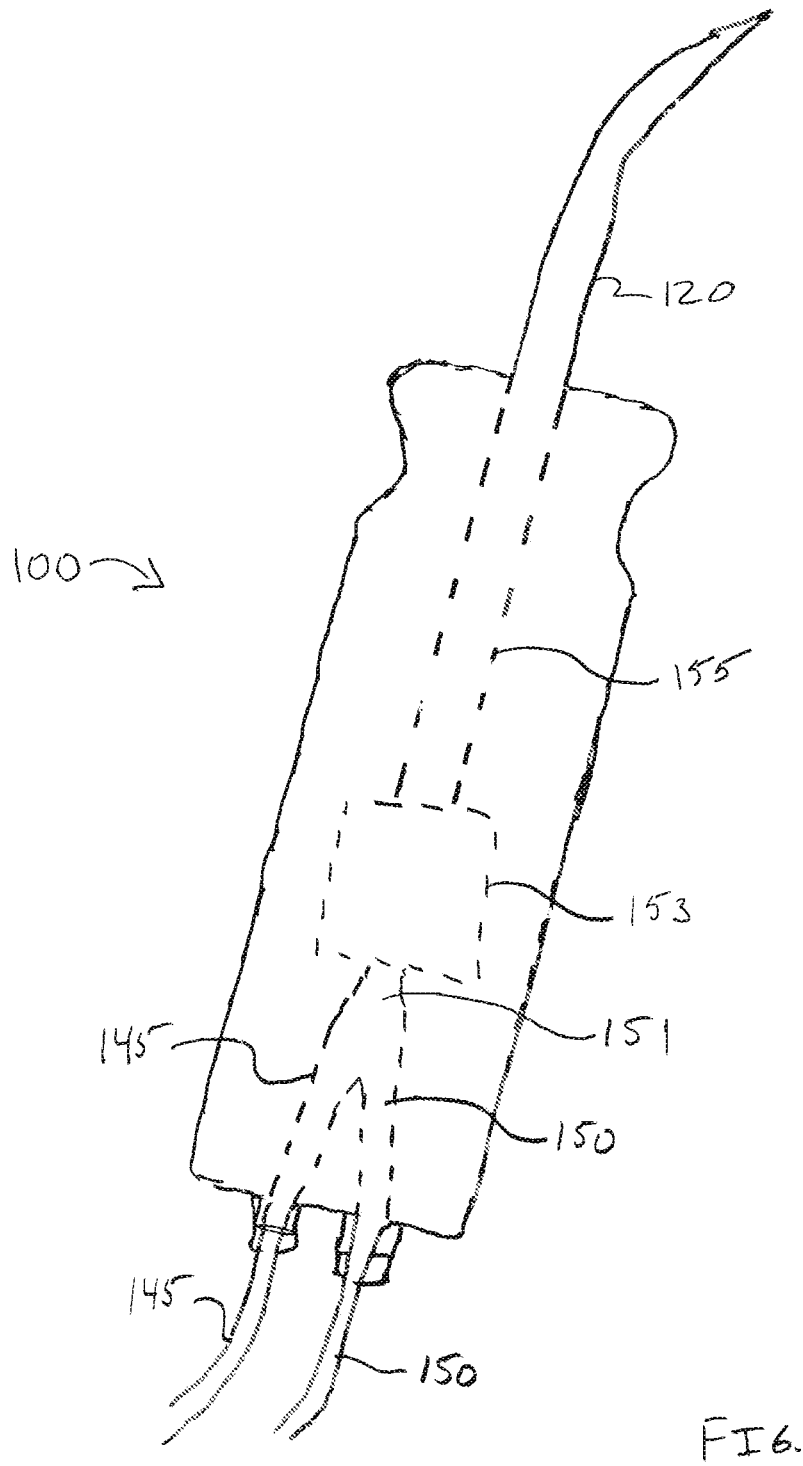

Referring in to FIGS. 1 and 1A, in this embodiment, the first (145) and second (150) supply tubes merge into a single lumen 151 within the interior of the handle body 105. The lumen 151 connects to a pump 153 within the handle body 105 capable of receiving the fluid from the lumen 151 and expelling it into a second lumen 155 that extends to a distal nozzle body 120 under pressure. The nozzle body 120 discharges the cleansing supply (or water) alone, or in combination with any soap, disinfecting solution, or other cleaning chemicals supplied by the second supply tube 150. The nozzle body 120 can be any desirable length as denoted in FIG. 1 and can be configured in any shape according to preference. In general, the first supply tube 145 can be connected to a water source—which can be a plumbed water supply, a reservoir, or any other type of storage tank. Similarly, the second supply tube 150 can be connected to a storage container containing soaps, detergents, or disinfecting solutions.

In this embodiment, the water supply and the soap, detergent, or disinfecting solution can be provided to the handle body under pressure by auxiliary pumps or other mechanisms, including static water pressure. In this embodiment, the pump 153 is housed within the handle body 105 and is capable of producing a jet of water of from the distal tip 129 of the nozzle body 120 with sufficient energy to dislodge foreign materials from objects such as medical instruments and the like. The miniature pump can be any pump type known in the art that produces sufficient pressure for a particular cleaning activity.

In this embodiment, the nozzle body 120 includes a slight bend 125 as illustrated. The angle of the bend can be chosen so as to provide a desired level of comfort and convenience to the user when cleaning objects such as medical instruments. Although not depicted, it will be understood that the bend 125 can be configured in any shape, size or orientation to satisfy the needs of the user for any particular purpose. In one example, the bend 125 can be such that it allows a distal tip 129 of the nozzle body 120 to reach interior portions of objects such as medical devices that would normally be difficult to reach.

In this embodiment, the distal tip 129 of the nozzle body 120 is configured to create a jet of cleaning solution 131. In general, the characteristics of the jet can be configured for one or more purposes, e.g., the output velocity, cross-sectional diameter, focus, and other characteristics of the jet 131 can be adapted to clean certain types of surfaces, instruments, or other aspects.

In this embodiment, the handle body 105 further includes a toggle switch 160 that allows a user to select from two or more operating configurations. The toggle switch 160 can be coupled to an internal electronic control system (not shown in FIG. 1) that mechanically controls the jet output characteristics; alternatively, the toggle switch can be in signal communication with a remote pump (not shown in FIG. 1) that controls the jet output characteristics. In one example, the toggle switch 160 can allow a user to switch between low and high pressure jet 131 output settings. In another example, the toggle switch 160 can allow a user to switch between three different operating modes of the jet: straight stream, pulsed-low pressure, and pulsed-high pressure. Other operating modes will be apparent to those skilled in the art.

In this embodiment, a power cord 140 can supply requisite power for driving a pump, if the pump is integral with the handle (described below), powering electronic control devices, lights, and other features of the device 100. In some embodiments, the nozzle body 120 can include a distal light source 162 oriented at or near the distal tip 129 for the purpose of illuminating the target area of the object that the user is cleaning. The light source 162 can be any light source known in the art including, but not limited to light emitting diodes.

In this and other embodiments, a splash shield 170 can reduce the likelihood of foreign matter such as blood, bone, or tissue, cleansing soaps or chemicals splashing onto the user. The splash shield 170 can be reversibly coupled to the nozzle body 120, the handle body 105, or any other structure of the device 100 that provides a desired level of splash protection. Although the splash shield 170 is depicted as dome-shaped in FIG. 1, it will be understood that the shield can be configured in any shape or size to provide a desired level of splash protection for the user. In one embodiment, the splash shield can be constructed of a hydrophobic material, or include a hydrophobic outer layer to repel water and other water-based materials from adhering to its surface. Such a configuration can allow a user to clearly visualize a target area of an instrument while cleaning.

In this and other embodiments, the handle body 105 can be disassembled for one or more of cleaning, disinfection, or sterilization. Alternatively, in some embodiments, the nozzle body 120 can be removed separately for the same purpose.

Referring now to FIGS. 2A-2E, in this and other embodiments, the handle body 105 can accommodate interchangeable nozzle bodies. For example, a user can swap a first nozzle body that provides a first jet 131 pattern for a second, different nozzle body that provides a different jet pattern and vice-versa. In one embodiment, the handle body 105 can include an interiorly-threaded bore 185 configured to correspondingly receive an exteriorly-threaded distal portion 121 of a nozzle 120 at the distal end 175 of the handle body as specifically illustrated in FIG. 2D. The bore 185 can be in fluid communication with the second lumen 155 such that fluid can flow from the second lumen 155 into the bore 185 and subsequently into the nozzle 120. In this embodiment, a nozzle can be removed from, or attached to the handle body by screwing the threaded portions together. It will be understood that other coupling mechanisms can be employed for this and other purposes.

Figure 2A:
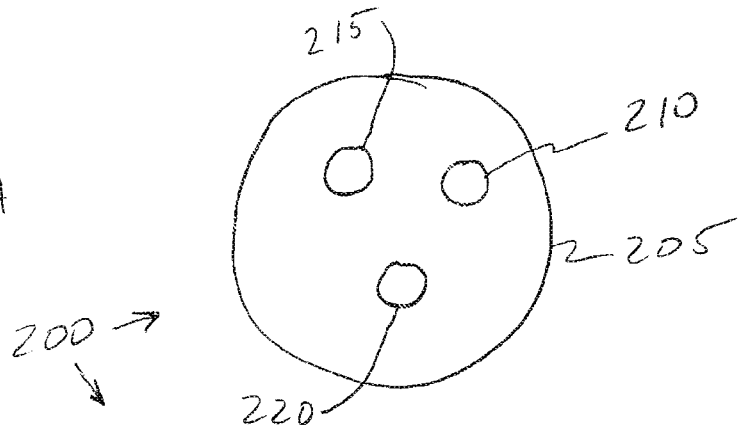
FIGS. 2A-2E illustrate a variety of nozzle attachments according to multiple embodiments.
Figure 2B:
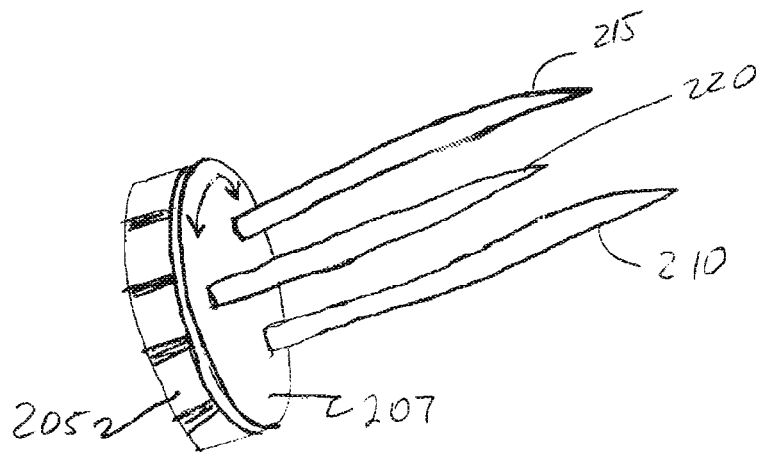
Figure 2C:
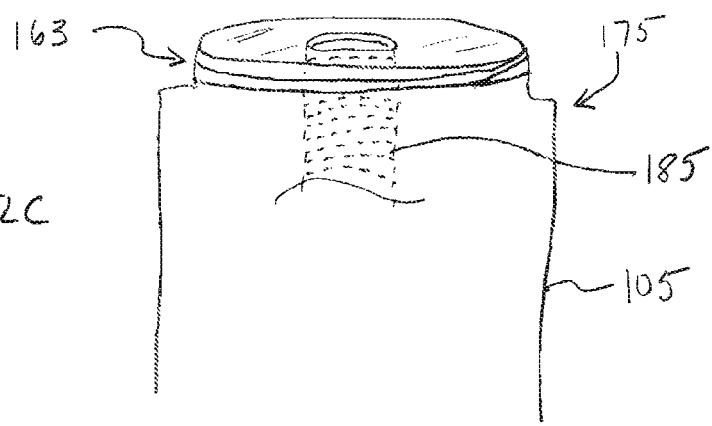
Figure 2D:
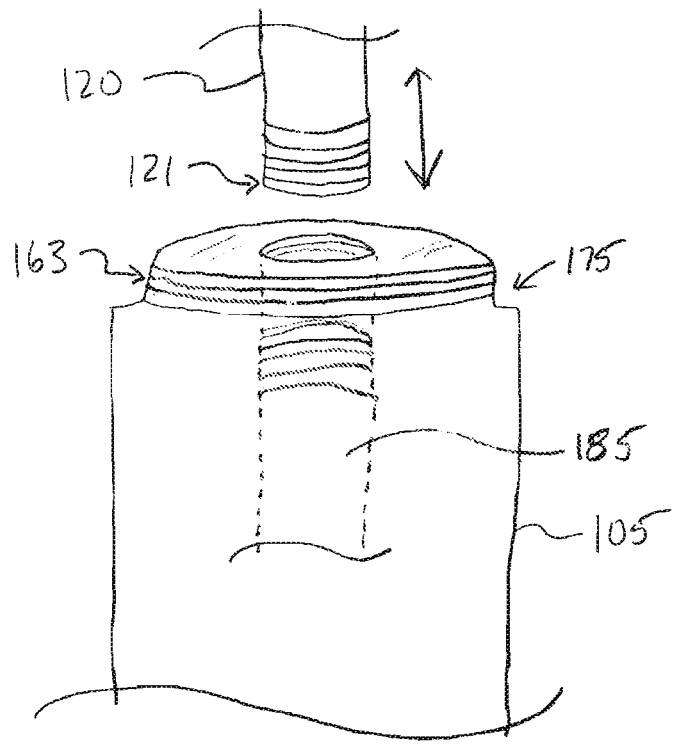
Figure 2E:
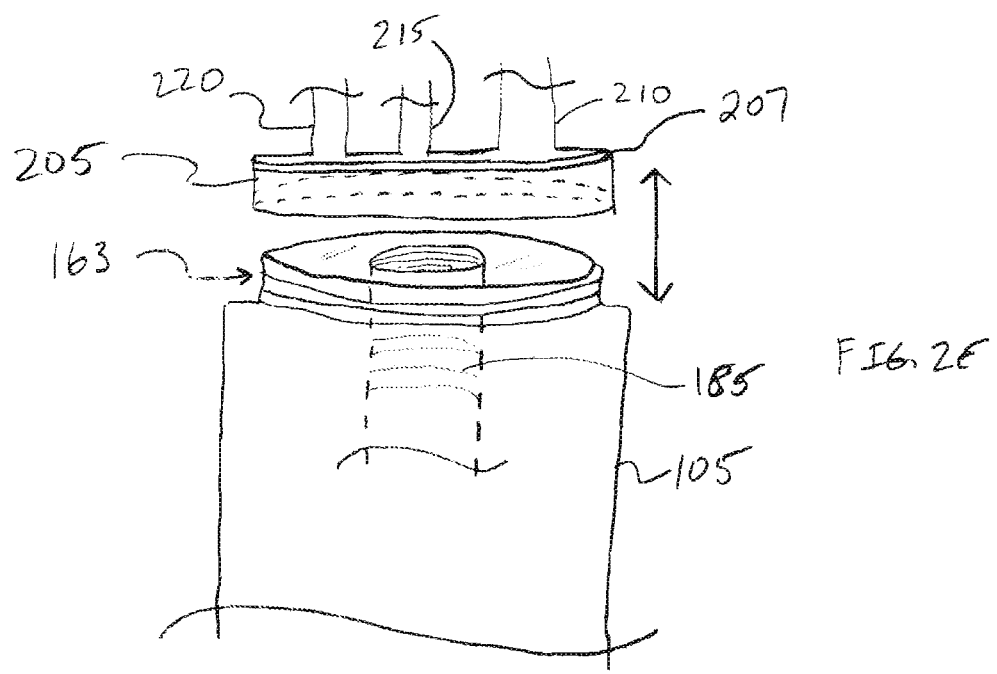

In one embodiment, the handle body 105 can be configured to reversibly couple to a nozzle turret 200 to allow a user to select from a plurality of different nozzle types. FIGS. 2A and 2B illustrate one embodiment of a nozzle turret 200 shown in top- and isometric views, respectively. In this embodiment, the nozzle turret 200 includes an interiorly-threaded turret body 205 that can be coupled to a corresponding exteriorly-threaded collar portion 163 of the nozzle body 105 as specifically shown in FIG. 2E. The nozzle turret 200 can allow a user to select from three different nozzles, 210, 215, 220, respectively, by rotating a plate member 207 into a position that aligns the bore 185 of the handle body 105 with one of the three nozzles. In this embodiment, each of the nozzles 210, 215, 220 can produce a different jet pattern or otherwise provide different jet characteristics. For example, nozzle 210 may produce a straight-stream jet; nozzle 215 may produce a fan-shaped stream; and nozzle 215 may produce a spray pattern, each of which can be selected by the user by orienting the nozzle turret on the handle body accordingly. It will be understood that while the bore 185 is illustrated as being centrally-disposed in the handle body 105, the bore 185 can be offset to allow activation of a selected nozzle when using a nozzle turret. Components for selectably activating a nozzle in a nozzle turret are not shown for figure clarity. In one embodiment, the plate member 207 includes gaskets, seals, and other plumbing components necessary to allow the plate member 207 to be rotated into a selected position such that only one of the selected nozzles 210, 215, 220 produces a jet output.

In one embodiment, the handle body 105 can include a second toggle switch (not shown in FIG. 1 or 2) that allows a user to switch between a water jet, a blended water/soap solution jet, and a pure soap or disinfecting solution jet. Accordingly, a user can, for example, clean an instrument with a desired amount of cleaning or soap solution, then rinse the cleaning or soap solution using water only.

In general, a cleaning device of the type described herein can be advantageously used for cleaning medical devices. Medical devices such as surgical instruments commonly include small crevices, cracks, notches, or other structures that can harbor foreign matter such as blood, bone and bone fragments, tissue, and other bodily matter. In one use of a device of the type described herein, a user can activate the device to produce a fine, but powerful jet of water capable of dislodging foreign matter from surgical instruments. In those embodiments that include interchangeable nozzles, or a nozzle turret of the type described herein, a user can change the nozzle to produce a selected jet pattern for reaching small, hidden, or hard-to-reach areas of the medical instrument for the purpose of cleaning the instrument.

A number of illustrative embodiments have been described. Nevertheless, it will be understood that various modifications may be made without departing from the spirit and scope of the various embodiments presented herein. Accordingly, other embodiments are within the scope of the following claims.

What is claimed is:

1. A hand-held cleaning system for removing foreign bodies from a contaminated medical device, comprising:
    a hand-held pump housing comprising:
        an electrically-driven internal pump configured to receive a cleansing solution at an inlet port from an inlet lumen and pump said cleansing solution through an outlet port to an elongate nozzle body that protrudes from said pump housing; and
        exteriorly-disposed user controls operable to vary the force with which said cleansing solution is pumped to said elongate nozzle body;
    wherein said nozzle body is configured to produce an output jet of said cleansing solution for forcefully removing said foreign bodies from small structural features of said contaminated medical device;
    wherein said pump housing is sized to provide the capability of intricately removing said foreign bodies from said contaminated medical device via said output jet and manipulate said user controls with one hand; and
    wherein a distal end portion of said inlet lumen is separately in fluid communication with a water source and a composition formulated to clean or disinfect said medical instrument, and a proximal end portion is in fluid communication with said inlet port of said pump.

2. The cleaning system of claim 1, wherein said elongate nozzle body is configured for cleaning said foreign bodies from a hand-operated medical or dental surgery instrument.

3. The cleaning system of claim 1, wherein said nozzle body is configured to produce a jet of said cleansing solution having a jet cross-diameter from about 0.25 mm to about 5.0 mm.

4. The cleaning system of claim 2, wherein said instrument is a scalpel, saw, drill bit, clamp, forceps, tweezers, retractor, needle driver, hemostat, scissors, catheter, mirror, probe, bur, excavator, burnisher, scaler, prosthodontic, elevator, or chisel.

5. The cleaning system of claim 1, wherein said pump housing is configured to reversibly couple with one of a plurality of nozzle bodies, each nozzle body being configured to produce a jet having a jet characteristic that is unique with respect to the jet characteristics of the others of said plurality of nozzle bodies.

6. The cleaning system of claim 5, wherein said pump housing comprises a shoulder body on a distal end portion having a threaded bore configured to threadingly engage a correspondingly threaded proximal end portion of said nozzle body.

7. The cleaning system of claim 6, wherein said shoulder body further comprises a circumferentially threaded wall member configured to threadingly engage a cap body of a nozzle turret, wherein said cap body comprises an inner wall having a complimentary thread to allow said cap body to be reversibly coupled to said shoulder body through twisting motion.

8. The cleaning system of claim 7, wherein said nozzle turret comprises said cap body, and a plurality of unique nozzle bodies extending substantially perpendicularly from said cap body, wherein said nozzle turret is configured to allow said cleansing solution to flow through a selected one of said plurality of said nozzle bodies to produce said jet.

9. The cleaning system of claim 8, wherein said plurality of nozzle bodies comprises a first nozzle body configured to produce a straight stream; a second nozzle body configured to produce a fan-stream; and a third nozzle body configured to produce a pulsating straight stream.

10. The cleaning system of claim 5, wherein said nozzle body comprises a progressively narrowing interior lumen extending from a proximal portion of said nozzle body to a distal portion of said nozzle body where said jet emerges from said nozzle body.

11. The cleaning system of claim 1, wherein said nozzle body is resiliently flexible.

12. The cleaning system of claim 5, wherein said nozzle body comprises a bend between the angles of about ninety (90) degrees and about thirty (30) degrees.

13. The cleaning system of claim 1, wherein said pump housing or said nozzle body is configured to receive a reversibly-attachable splash guard configured to confine splashing of said cleansing solution or said foreign contaminants to the area of said nozzle body.

14. The cleaning system of claim 13, wherein said splash guard is a dome-shaped shield configured to reversibly attach to said nozzle body wherein a concave side of said shield faces a distal tip of said nozzle body.

15. The cleaning system of claim 1, further comprising one or more selector bodies operably configured on said pump housing to control one or more of: the resulting temperature of said jet, the resulting force of said jet, or the concentration of said cleaning agent in said cleansing solution.

16. The cleaning system of claim 15, wherein said one or more selector bodies is configured to selectively allow a user to choose between:
    a wash setting, wherein said jet is comprised of water and said cleansing agent mixed in a selected ratio;
    a rinse setting, wherein said jet is comprised of water only; and
    a pulse setting, wherein said jet is comprised of either water only, or water plus said cleansing agent, and said jet is produced in a pulsating stream.

* * * * *